United States Patent [19]
McClelland et al.

[11] Patent Number: 5,849,699
[45] Date of Patent: Dec. 15, 1998

[54] SOLUBLE MOLECULE RELATED TO BUT DISTINCT FROM ICAM-1

[75] Inventors: Alan McClelland, Old Saybrook; Jeffrey M. Greve, Branford, both of Conn.

[73] Assignee: Bayer Corporation, West Haven, Conn.

[21] Appl. No.: 425,989

[22] Filed: Apr. 20, 1995

Related U.S. Application Data

[63] Continuation of Ser. No. 156,653, Nov. 22, 1993, abandoned, which is a continuation of Ser. No. 5,204, Jan. 15, 1993, abandoned, which is a continuation of Ser. No. 449,356, Dec. 21, 1989, abandoned, which is a continuation-in-part of Ser. No. 301,192, Jan. 24, 1989, Pat. No. 5,235,049, and Ser. No. 445,951, Dec. 13, 1989, abandoned.

[51] Int. Cl.$^6$ .......................... A61K 38/17; C07K 14/705
[52] U.S. Cl. .............................................. 514/12; 530/350
[58] Field of Search ................................ 530/350; 514/12

[56] References Cited

FOREIGN PATENT DOCUMENTS

| | | |
|---|---|---|
| 0169146 | 1/1986 | European Pat. Off. . |
| 0289949 | 11/1988 | European Pat. Off. . |
| 0314863 | 5/1989 | European Pat. Off. . |
| 0319815 | 6/1989 | European Pat. Off. . |
| 0365837A2 | 5/1990 | European Pat. Off. . |

OTHER PUBLICATIONS

Staunton et al 1989 Cell 56(5):849–853.
Cole et al. 1986. Topographic local of leparin binding domain of the NCAM. J. Cell Biol. 103 1739–1744.
Gussow & Pleogh, 1987, Soluble class/outigens: a conundrum with no solutions? Immunol Today 8:220.
Scopes, R.R. Protein Protein Purification: Principles and Practice.
Springer–Verlag, new york 1982, pp. 39–43.
Bothlein et al. 1986. A human ICAM–1 distinct from F7A–1 J. Immunol. 137:1270–1274.
Marlin & Springer, 1987. Purified ICAM–1 is a ligend for lymphocyte function associated antigen 1. *Cell* 51:813–819.
Gough. 1987. Putting a stop to an immunoglobulin message, Trends in Genet. 3:238.
Staunton et al. 1988. Primary structure of ICAM–1 demon. interact. betw. members of the Immunogl. & Integrin Supergene Families Cell 52:925–933.
Bock et al 1987. Characterization of soluble forms of NCAM FEBS letters 255:33.
Gower et al 1988. Alternative Splicing Generates a Secreted form of NCAM in muscle and brain. Cell 55:955.
Simmons et al 1988. ICAM, an adhesion ligand of LFA–1, is homol. to NCAM. Nature 331:624–627.
Cunningham et al. Neural Cell Adhesion Molecule: Structure, Immuno. like Domains, Cell surf. Mod., and Alt. RNA Spl. Science, 236:799.
Journal of Virology, vol. 58, No. 2, May 1986, pp. 290–295, J.E. Tomassini et al.; Isolation of a receptor protein involved in attachment of human rhinoviruses.

*Primary Examiner*—Stephen Walsh
*Assistant Examiner*—Karen E. Brown

[57] ABSTRACT

The present invention relates to a soluble form of intercellular adhesion molecule (sICAM-1) and purified and isolated human sICAM-1. This invention also relates to a purified and isolated DNA sequence encoding sICAM-1. The extracellular domain of sICAM-1 and insoluble ICAM-1 are substantially the same. ICAM-1 is involved in the process through which lymphocytes attach to cellular substrates during inflammation and serves as the major human rhinovirus receptor (HRR). sICAM-1 therefore has both the property of reducing immune inflammation and inhibiting infection of rhinovirus and Coxsackie A virus.

3 Claims, 8 Drawing Sheets

| | | |
|---|---|---|
| 58 | ATGGCTCCCAGCAGCCCCCGGCCCGCGCTGCCCGCACTCCTGGTCCTGCTCGGGGCTCTG | 117 |
| | M A P S S P R P A L P A L L V L L G A L | |
| 118 | TTCCCAGGACCTGGCAATGCCCAGACATCTGTGTCCCCCTCAAAAGTCATCCTGCCCCGG | 177 |
| | F P G P G N A Q T S V S P S K V I L P R | 13 |
| 178 | GGAGGCTCCGTGCTGGTGACATGCAGCACCTCCTGTGACCAGCCCAAGTTGTTGGGCATA | 237 |
| | G G S V L V T C S T S C D Q P K L L G I | 33 |
| 238 | GAGACCCCGTTGCCTAAAAAGGAGTTGCTCCTGCCTGGGAACAACCGGAAGGTGTATGAA | 297 |
| | E T P L P K K E L L L P G N N R K V Y E | 53 |
| 298 | CTGAGCAATGTGCAAGAAGATAGCCAACCAATGTGCTATTCAAACTGCCCTGATGGGCAG | 357 |
| | L S N V Q E D S Q P M C Y S N C P D G Q | 73 |
| 358 | TCAACAGCTAAAACCTTCCTCACCGTGTACTGGACTCCAGAACGGGTGGAACTGGCACCC | 417 |
| | S T A K T F L T V Y W T P E R V E L A P | 93 |
| 418 | CTCCCCTCTTGGCAGCCAGTGGGCAAGAACCTTACCCTACGCTGCCAGGTGGAGGGTGGG | 477 |
| | L P S W Q P V G K N L T L R C Q V E G G | 113 |
| 478 | GCACCCCGGGCCAACCTCACCGTGGTGCTGCTCCGTGGGGAGAAGGAGCTGAAACGGGAG | 537 |
| | A P R A N L T V V L L R G E K E L K R E | 133 |
| 538 | CCAGCTGTGGGGGAGCCCGCTGAGGTCACGACCACGGTGCTGGTGAGGAGAGATCACCAT | 597 |
| | P A V G E P A E V T T T V L V R R D H H | 153 |
| 598 | GGAGCCAATTTCTCGTGCCGCACTGAACTGGACCTGCGGCCCCAAGGGCTGGAGCTGTTT | 657 |
| | G A N F S C R T E L D L R P Q G L E L F | 173 |
| 658 | GAGAACACCTCGGCCCCCTACCAGCTCCAGACCTTTGTCCTGCCAGCGACTCCCCCACAA | 717 |
| | E N T S A P Y Q L Q T F V L P A T P P Q | 193 |
| 718 | CTTGTCAGCCCCCGGGTCCTAGAGGTGGACACGCAGGGGACCGTGGTCTGTTCCCTGGAC | 777 |
| | L V S P R V L E V D T Q G T V V C S L D | 213 |
| 778 | GGGCTGTTCCCAGTCTCGGAGGCCCAGGTCCACCTGGCACTGGGGGACCAGAGGTTGAAC | 837 |
| | G L F P V S E A Q V H L A L G D Q R L N | 233 |

FIG. 1A

| | | |
|---|---|---|
| 838 | CCCACAGTCACCTATGGCAACGACTCCTTCTCGGCCAAGGCCTCAGTCAGTGTGACCGCA | 897 |
| | P  T  V  T  Y  G  N  D  S  F  S  A  K  A  S  V  S  V  T  A | 253 |
| 898 | GAGGACGAGGGCACCCAGCGGCTGACGTGTGCAGTAATACTGGGGAACCAGAGCCAGGAG | 957 |
| | E  D  E  G  T  Q  R  L  T  C  A  V  I  L  G  N  Q  S  Q  E | 273 |
| 958 | ACACTGCAGACAGTGACCATCTACAGCTTTCCGGCGCCCAACGTGATTCTGACGAAGCCA | 1017 |
| | T  L  Q  T  V  T  I  Y  S  F  P  A  P  N  V  I  L  T  K  P | 293 |
| 1018 | GAGGTCTCAGAAGGGACCGAGGTGACAGTGAAGTGTGAGGCCCACCCTAGAGCCAAGGTG | 1077 |
| | E  V  S  E  G  T  E  V  T  V  K  C  E  A  H  P  R  A  K  V | 313 |
| 1078 | ACGCTGAATGGGGTTCCAGCCCAGCCACTGGGCCCGAGGGCCCAGCTCCTGCTGAAGGCC | 1137 |
| | T  L  N  G  V  P  A  Q  P  L  G  P  R  A  Q  L  L  L  K  A | 333 |
| 1138 | ACCCCAGAGGACAACGGGCGCAGCTTCTCCTGCTCTGCAACCCTGGAGGTGGCCGGCCAG | 1197 |
| | T  P  E  D  N  G  R  S  F  S  C  S  A  T  L  E  V  A  G  Q | 353 |
| 1198 | CTTATACACAAGAACCAGACCCGGGAGCTTCGTGTCCTGTATGGCCCCCGACTGGACGAG | 1257 |
| | L  I  H  K  N  Q  T  R  E  L  R  V  L  Y  G  P  R  L  D  E | 373 |
| 1258 | AGGGATTGTCCGGGAAACTGGACGTGGCCAGAAAATTCCCAGCAGACTCCAATGTGCCAG | 1317 |
| | R  D  C  P  G  N  W  T  W  P  E  N  S  Q  Q  T  P  M  C  Q | 393 |
| 1318 | GCTTGGGGGAACCCATTGCCCGAGCTCAAGTGTCTAAAGGATGGCACTTTCCCACTGCCC | 1377 |
| | A  W  G  N  P  L  P  E  L  K  C  L  K  D  G  T  F  P  L  P | 413 |
| 1378 | ATCGGGGAATCAGTGACTGTCACTCGAGATCTTGAGGGCACCTACCTCTGTCGGGCCAGG | 1437 |
| | I  G  E  S  V  T  V  T  R  D  L  E  G  T  Y  L  C  R  A  R | 433 |
| 1438 | AGCACTCAAGGGGAGGTCACCCGCAAGCCCCCGGTATGAGATTGTCATCATCACTGTGG | 1497 |
| | S  T  Q  G  E  V  T  R  K  P  P  G  M  R  L  S  S  S  L  W | 453 |
| 1498 | TAG | 1500 |
| | * | |

FIG. 1B

COMPARISON OF C-TERMINAL REGIONS OF ICAM-1 AND sICAM-1

```
1441  ACTCAAGGGGAGGTCACCCGCAAGGTGACCGTGAATGTGCTCTCCCCCCGGTATGAGATT
 435   T  Q  G  E  V  T  R  K  V  T  V  N  V  L  S  P  R  Y  E  I

1441  ACTCAAGGGGAGGTCACCCGCAAG-------------------CCCCCCGGTATGAGATT
 435   T  Q  G  E  V  T  R  K                    P  P  G  M  R  L

1501  GTCATCATCACTGTGGTAGCAGCCGCAGTCATAATGGGCACTGCAGGCCTCAGCACGTAC
 455   V  I  I  T  V  V  A  A  A  V  I  M  G  T  A  G  L  S  T  Y

1482  GTCATCATCACTGTGGTAGCAGCCGCAGTCATAATGGGCACTGCAGGCCTCAGCACGTAC
 449    S  S  S  L  W  *

1561  CTCTATAACCGCCAGCGGAAGATCAAGAAATACAGACTACAACAGGCCCAAAAAGGGACC
 475   L  Y  N  R  Q  R  K  I  K  K  Y  R  L  Q  Q  A  Q  K  G  T

1542  CTCTATAACCGCCAGCGGAAGATCAAGAAATACAGACTACAACAGGCCCAAAAAGGGACC

1621  CCCATGAAACCGAACACACAAGCCACGCCTCCCTGAACCTATCCCGGGACAGGGCCTCTT
 495   P  M  K  P  N  T  Q  A  T  P  P  *

1602  CCCATGAAACCGAACACACAAGCCACGCCTCCCTGAACCTATCCCGGGACAGGGCCTCTT
```

UPPER LINES: ICAM-1 cDNA SEQUENCE AND TRANSLATION
LOWER LINES: sICAM-1 cDNA SEQUENCE AND TRANSLATION

FIG.2

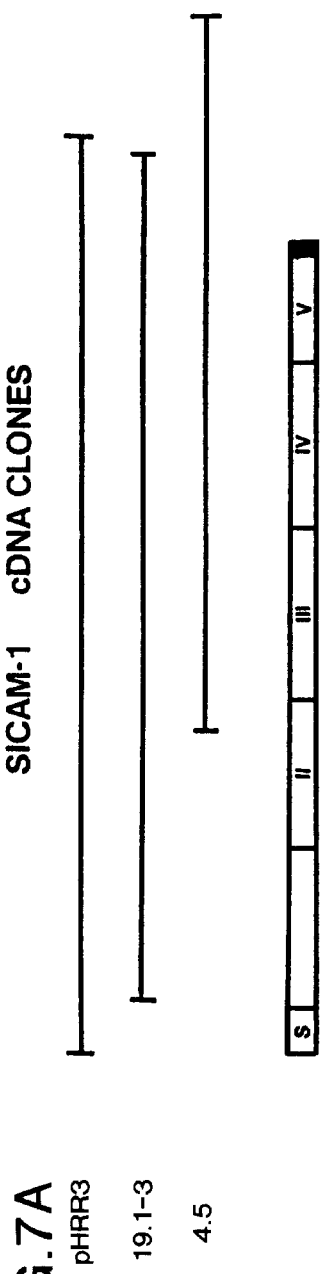
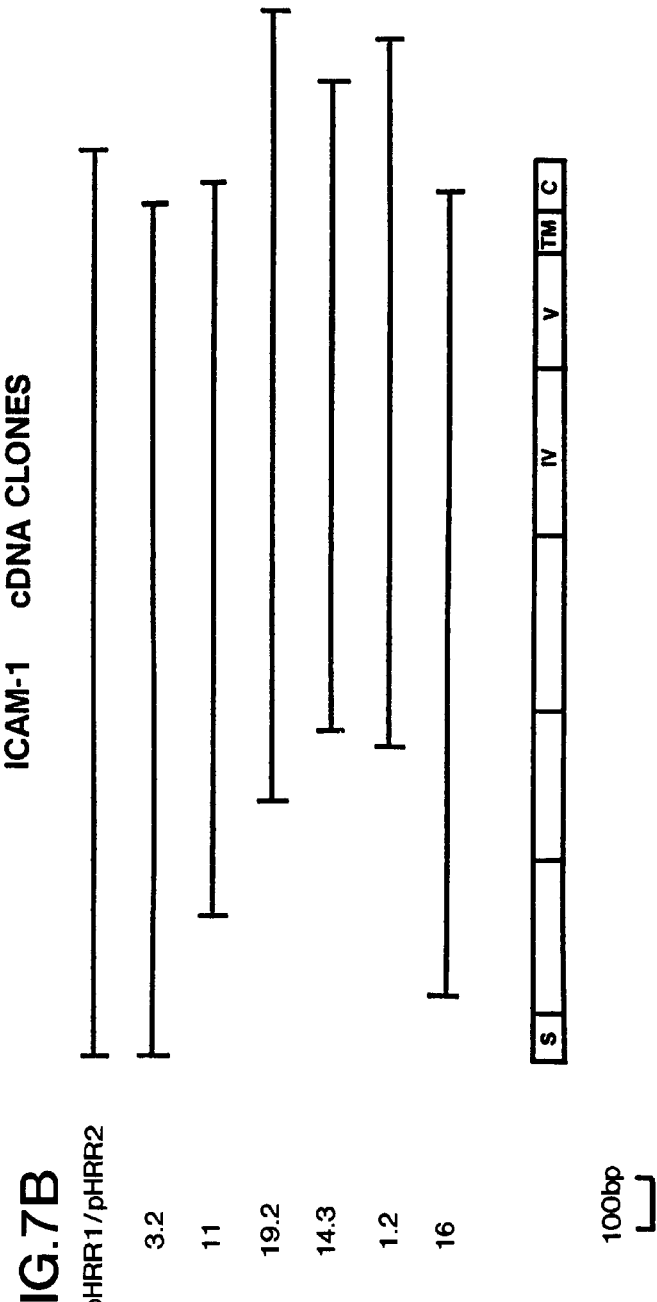

SOLUBLE MOLECULE RELATED TO BUT DISTINCT FROM ICAM-1

This is a continuation of application U.S. Ser. No. 08/156,653, filed on Nov. 22, 1993, now abandoned, which is a continuation of U.S. Ser. No. 08/005,204, filed Jan. 15, 1993, now abandoned, which is a continuation of U.S. Ser. No. 07/449,356, filed Dec. 21, 1989, now abandoned, which is a continuation-in-part of U.S. Ser. No. 07/301,192, filed Jan. 24, 1989, which issued as U.S. Pat. No. 5,235,049 on Aug. 10, 1993, and a continuation-in-part of U.S. Ser. No. 07/445,951, filed Dec. 13, 1989.

BACKGROUND OF THE INVENTION

The present invention relates to a soluble form of intercellular adhesion molecule (sICAM-1) as well as the DNA sequence encoding sICAM-1. sICAM-1 and ICAM-1 have substantial similarity, in that they share the first 442 NH 2-terminal amino acids of the extracellular domain. However, sICAM-1 differs from ICAM-1 at the C-terminus., and these changes confer solubility to sICAM-1. ICAM-1 is known to mediate adhesion of many cell types, including endothelial cells, to lymphocytes which express lymphocyte function-associated antigen-1 (LFA-1). ICAM-1 has the property of directly binding LFA-1. There is also evidence for LFA-1 mediated adhesion which is not via ICAM-1. Additionally, ICAM-1 has the ability to bind both LFA-1 and human rhinovirus. It has the property of inhibiting infection of rhinovirus and Coxsackie A viruses. It may be used to antagonize adhesion of cells mediated by ICAM-1 binding including ICAM-1/LFA-1 binding and thus be useful in treatment of inflammation, graft rejection, LFA-1 expressing tumors, and other processes involving cell adhesion. Based on the substantial similarity of the extracellular domains of ICAM-1 and sICAM-1, sICAM-1 has the properties identified for ICAM-1.

The major Human Rhinovirus Receptor (HRR) has been transfected, identified, purified and reconstituted as described in co-pending U.S. patent applications Ser. No. 262570 and 262428 filed Oct. 25, 1988 both now abandoned. This receptor has been shown to be identical to a previously described cell surface protein, ICAM-1. European Patent Application 0 289 949 describes a membrane associated cell adhesion molecule (ICAM-1) which mediates attachment of many cell types including endothelial cells to lymphocytes which contain LFA-1. This patent application provides a discussion of the present research in the field of intercellular adhesion molecules. It is important to note that the inventors specifically looked for an alternatively spliced mRNA for ICAM-1 and did not identify one. ICAM-1 was first identified based on its role in adhesion of leukocytes to T-cells (Rothlein, R. et al *J. Immunol.* 137: 1270–1274 (1986)) which has been shown to be mediated by the heterotypic binding of ICAM-1 to LFA-1 (Marlin et al, *Cell* 51: 813–819 (1987)). The primary structure of ICAM-1 has revealed that it is homologous to the cellular adhesion molecules Neural Cell Adhesion Molecule (NCAM) and Mylein-Associated Glycoprotein (MAG), and has led to the proposal that it is a member of the immunoglobulin supergene family (Simmons et al, *Nature* 331: 624–627 (1988); Staunton et al, *Cell* 52: 925–933 (1988) The DNA sequence of cDNA clones are described in the above referenced papers by Simmons et al and Staunton et al, supra, from which the amino acid sequence of ICAM-1 can be deduced. The ICAM-1 molecule has a typical hydrophobic membrane spanning region containing 24 amino acids and a short cytoplasmic tail containing 28 amino acids. The ICAM-1 of the prior art is an insoluble molecule which is solubilized from cell membranes by lysing the cells in a non-ionic detergent. The solubilized ICAM-1 mixture in detergent is then passed through a column matrix material and then through a monoclonal antibody column matrix for purification.

SUMMARY OF THE INVENTION

The present invention provides an endogenous alternatively spliced molecular species of ICAM-1 designated sICAM-1 which displays an alternative MRNA sequence and which is soluble without the addition of a detergent.

The present invention provides purified and isolated human soluble intercellular adhesion molecule (sICAM-1), or a functional derivative thereof, substantially free of natural contaminants. sICAM-1 can be obtained from HeLa, He1 and primary transfectant cells thereof characterized by being soluble in the absence of nonionic detergents and being the translation product defined by a novel mRNA sequence. This natural product of human cells has the advantage of being secreted from cells in a soluble form and not being immunogenic. The natural soluble product differs from the natural insoluble product in that the soluble product contains a novel sequence of 11 amino acid residues at the C-terminus and does not contain the membrane spanning and cytoplasmic domains present in the insoluble form.

The present invention provides a purified and isolated DNA sequence encoding sICAM-1 as well as a host cell encoding said sequence.

The present invention provides a method of recovering soluble intercellular adhesion molecule in substantially pure form comprising the steps of:

(a) removing the supernatant from unlysed cells, (b) introducing the supernatant to an affinity matrix containing immobilized antibody capable of binding to sICAM-1, (c) permitting said sICAM-1 to bind to said antibody of said matrix, (d) washing said matrix to remove unbound contaminants, and (e) recovering said sICAM-1 in substantially pure form by eluting said sICAM-1 from said matrix.

Further purification utilizing a lectin or wheat germ agglutinin column may be used before or after the antibody matrix step. Other purification steps could include sizing chromatography, ion chromatography, and gel electrophoresis. Further purification by velocity sedimentation through sucrose gradients may be used. The antibody capable of binding to sICAM-1 could include antibodies against ICAM-1 or HRR.

The present invention includes polyclonal antibodies against sICAM-1.

The present invention further includes an antibody specific for sICAM-1, capable of binding to the sICAM-1 molecule and that is not capable of binding to ICAM-1. For a method for producing a peptide antisera see Green et al, Cell 28: 477–487 (1982).

The invention also includes a hybridoma cell line capable of producing such an antibody.

This invention further includes the therapeutic use of antibodies specifically directed to sICAM-1 to increase the adhesion of cells mediated by ICAM-1 and LFA-1.

The invention further includes a method for producing an antibody which is capable of binding to sICAM-1 and not to ICAM-1 comprising the steps of (a) preparing a peptide-protein conjugate said peptide-protein conjugate specific to at least a portion of the unique 11 amino acid sequence present in sICAM-1, (b) immunizing an animal with said peptide-protein conjugate, (c) boosting the animals, and (d) obtaining the antisera.

The antibodies would be capable of binding to sICAM-1 and not capable of binding to ICAM-1. The invention includes the hybridoma cell line which produces an antibody of the same specificity, the antibody produced by the hybridoma cell and the method of production.

The invention further includes a method of inhibiting lymphocyte function associated antigen (LFA-1) and intercellular adhesion molecule-1 (ICAM-1) interaction comprising the step of contacting LFA-1 containing cells with sICAM-1 or a functional derivative thereof. This method of inhibition of ICAM-1 adhesion has application in such disease states as inflammation, graft rejection, and for LFA-1 expressing tumor cells.

This invention further includes a method of diagnosis of the presence and location of an LFA-1 expressing tumor cell.

This invention further includes a method for substantially reducing the infection of human rhinoviruses of the major receptor group comprising the step of contacting the virus with sICAM-1 or a functional derivative thereof.

BRIEF DESCRIPTION OF THE DRAWINGS

FIGS. 1A and 1B shows the nucleotide (SEQ ID NO: 10) and amino acid (SEQ ID NO: 11) sequence of sICAM-1.

FIG. 2 is a comparision of the C-terminal regions of sICAM-1 and ICAM-1. The nucleotide (SEQ ID NO: 12) and deduced amino acid (SEQ ID NO: 13) sequences of ICAM-1 and sICAM-1 (SEQ ID NO: 11) are shown beginning at amino acid residue 435. Dashes in the sICAM-1 sequence indicate missing nucleotides. The positions of the stop codons in both proteins are indicated by an asterisk.

FIG. 4A: Southern blot of HeLa (Lane 1), LTk– (Lane 2) and He1 (Lane 3) DNA restricted with Eco Ri and probed with the oligonucleotide ICAM-1.

FIGS. 7A and B are graphical representation of the cloned sICAM-1 and ICAM-1 plasmids.

FIG. 7A. pHRR3 is a full length cDNA encoding sICAM-1 obtained by PCR. Clones 19.1–3 and 4.5 are partial cDNA clones encoding sICAM-1 obtained from an He1 cDNA library in lambda GT11. Beneath the clones is a schematic of the sICAM-1 molecule. S denotes the signal peptide and I to V the IgG homologous domains. The solid box indicates the unique 11 amino acid C-terminus.

FIG. 7B. pHRR1 and pHRR2 are full length ICAM-1 cDNA clones obtained by PCR. The remaining ICAM-1 clones were obtained from an He1 cDNA library in lambda GT11. Beneath the clones is a schematic of the ICAM-1 molecule, showing the signal peptide (S), the five IgG homologous domains (I to V), the transmembrane region (TM) and the cytoplasmic domain (C).

DESCRIPTION OF THE PREFERRED EMBODIMENTS

Figure 3:
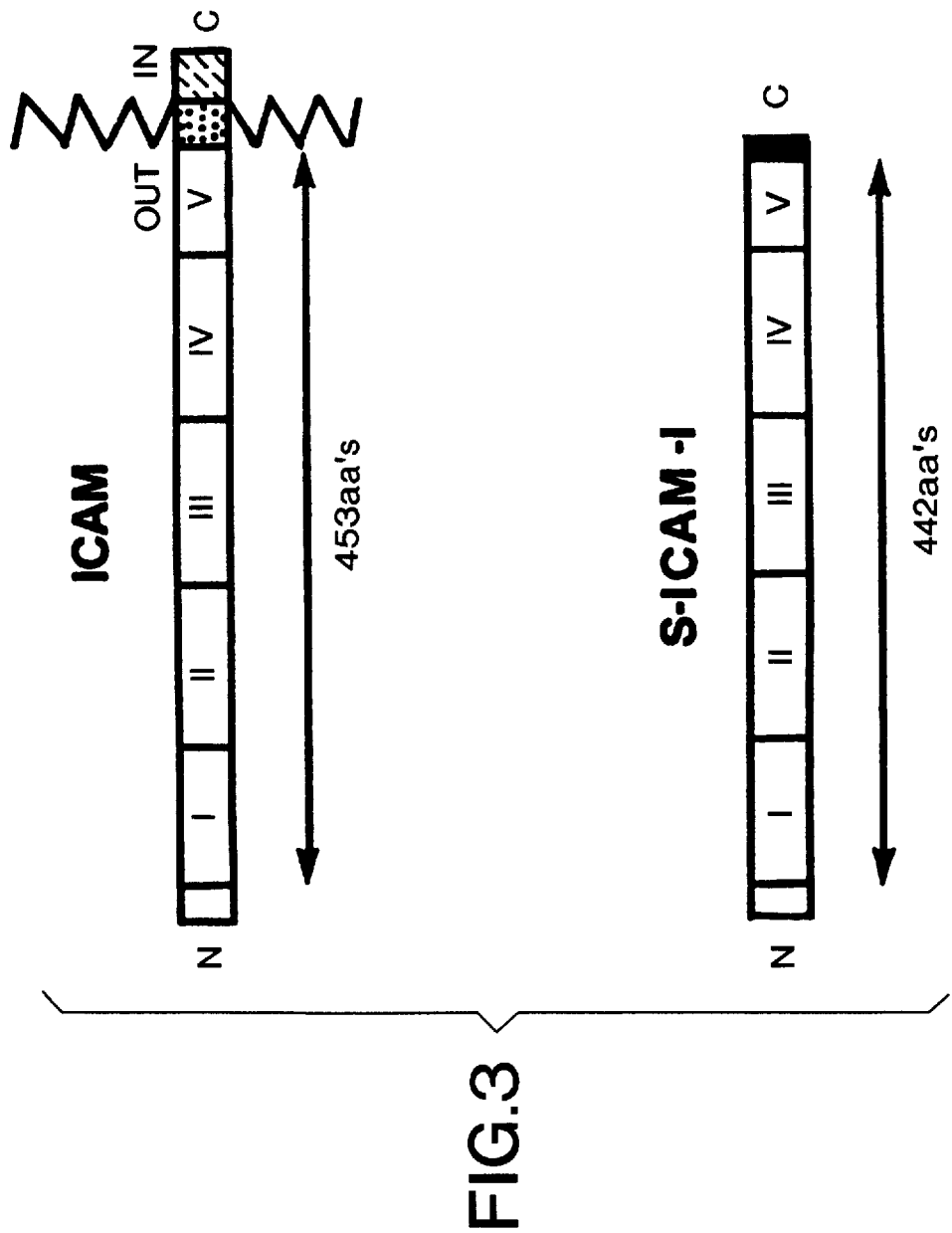
FIG. 3 is a comparison of the structure of sICAM-1 and ICAM-1. The membrane spanning region of ICAM-1 is indicated by the stippled box and the cytoplasmic domain by the hatched box. The novel C-terminus of sICAM-1 is indicated by the solid box. The five predicted domains showing homology with immunoglobulin are numbered I to V.

One aspect of the present invention relates to the discovery of a soluble natural binding ligand to the receptor binding site of Human Rhinovirus (HRV) and which also binds to LFA-1. This soluble natural molecule is related to but distinct from the molecule designated "Intercellular Adhesion Molecule-1" or "ICAM-1" which is insoluble, bound to the cell membrane and possesses a typical hydrophobic membrane spanning region and a short cytoplasmic tail. The novel protein of the present invention has a DNA sequence which includes a significant difference from the published DNA sequence for ICAM-1. sICAM-1 contains most of the extracellular domain of ICAM-1, which includes the functional domains for multiple functions including HRV and LFA-1 binding, but lacks the membrane spanning and cytoplasmic domains. sICAM-1 retains the ability to bind HRV and LFA-1 and is secreted in a soluble form. The DNA sequence for sICAM-1 contains a deletion of 19 base pairs from nucleotide 1465 to 1483 according to the numbering of Staunton et al, sudra (1988). The remainder of the sICAM-1 clone matches the published ICAM-1 sequence with the exception of a substitution of a A for G at nucleotide position 1462 which changes Glu 442 to Lys, as shown in FIG. 1B. The sequence of amino acid residues in a peptide is designated in accordance with standard nomenclature such as Lehninger's *Biochemistry,* Worth Publishers, New York, N.Y. (1970). sICAM-1 is a natural product of HeLa and He1 cells and other human cells which should have the property of binding to and inhibiting the infection of human rhinovirus and Coxsackie A viruses. It also has the property of binding to LFA-1 and may be used to antagonize adhesion of cells mediated by ICAM-1/LFA-1 binding and thus be useful as a therapeutic in treatment of inflammation, graft rejection, suppression of LFA-1 expressing tumor cells and other processes involving cell adhesion. Isolated and purified sICAM-1 protein as a therapeutic would not possess the immunogenic problems associated with foreign proteins. The secretion of a soluble naturally occurring protein eliminates the problems associated with production and purification of an insoluble, cell membrane bound protein, since cell lysis is not required and thus continuous culture can be employed as well as simplified procedures for purification and isolation of sICAM-1.

Non-human mammalian cell lines which express the major human rhinovirus receptor gene have been previously identified and are the subject matter of copending U.S. patent application Ser. No. 262570 and 262428 filed Oct. 25, 1988, both now abandoned, and include references to the ATCC deposits for the cell lines. The major human rhinovirus receptor was identified with monoclonal antibodies which inhibit rhinovirus infection. These monoclonal antibodies recognized a 95 kd cell surface glycoprotein on human cells and on mouse transfectants expressing a rhinovirus-binding phenotype. Purified 95 Kd protein binds to rhinovirus in vitro. Protein sequence from the 95 kd protein showed an identity with that of ICAM-1; a cDNA clone obtained from mouse transfectants expressing the rhinovirus receptor had the same sequence published for ICAM-1, except for the A for G change previously described. Thus it was determined that the major human rhinovirus receptor and ICAM-1 were the same protein. A transfected mouse L-cell line designated HEI had been isolated which contained and expressed the HRR gene or ICAM-1 gene. The ICAM-1 terminology has been used although it is now recognized that HRR and ICAM-1 are interchangeable.

A randomly primed cDNA library was prepared in lambda GT11 from He1 polyA+ RNA. The library was screened in duplicate using two oligonucleotides derived from the published sequence of ICAM-1. Oligonucleotide ICAM-1 has the sequence GAGGTGTTCTCAAACAGCTCCAGCCCT-TGGGGCCGCAGGTCCAGTTC SEQ ID NO: 5 and oligonucleotide ICAM-3 has the sequence CGTTGGCAGGA-CAAAGGTCTGGAGCTGGTAGGGGGCCGAGGTGTTCT SEQ ID NO: 6.

Eight positive clones were obtained from one screen and three were selected for further study. DNA sequencing of two of the clones showed identity with the published ICAM-1 sequence. The sequence of the third clone, lambda 19.1–3 was significantly different from the other two clones in that there was a deletion of 19 bp from nucleotide 1465 to 1483 according to the numbering of Staunton et al, supra. The 19 bp deletion was present in a second cDNA, lambda HE1–4.5 and independently confirmed using polymerase chain reaction (PCR) generated cDNA. Analysis of the cDNA sequence predicted the existence of a secreted form of ICAM-1 that is generated by an alternative splicing mechanism. Western blot identification of sICAM-1 from culture supernatants of He1 and HeLa cell lines confirm that the sICAM-1 MRNA sequence encodes a soluble form of ICAM-1 that does not associate with the cell surface but is released into the cell medium. An alternatively spliced MRNA generating a secreted form of another adhesion molecule (NCAM) has been identified (Glower et al, Cell 55:955–964 (1988)), although in NCAM an exon is incorporated into the mRNA while in the present invention an exon is deleted from the mRNA. No alternative mRNA sequence for ICAM-1 had previously been identified. (Staunton et al.)

sICAM-1 cDNA Clones

Figure 4A:
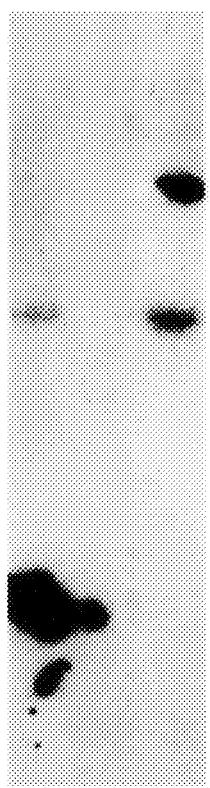
FIGS. 4A, B and C show the ICAM-1 gene and its expression in HRR transfectants.
Figure 4B:
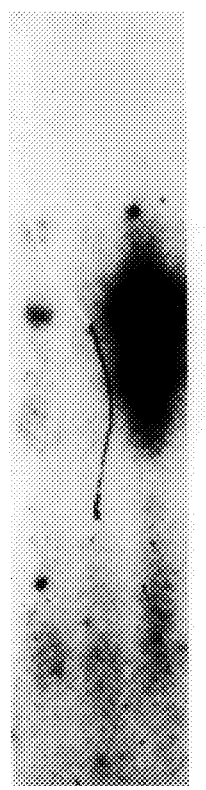
FIG. 4B: Northern blot of HeLa (Lane 1), Ltk– (Lane 2), and He1 (Lane 3). poly A+ RNA probed with the oligonucleotide ICAM-1.
Figure 4C:
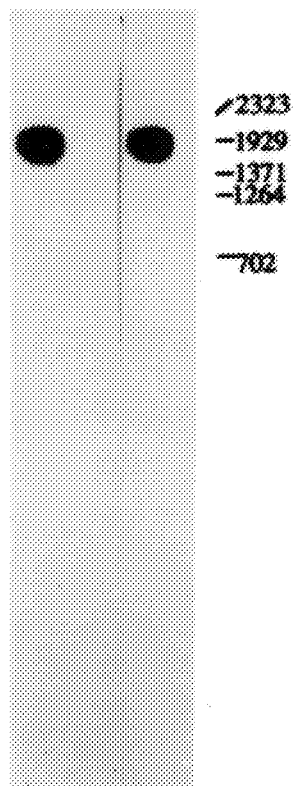
FIG. 4C: PCR amplification of CDNA prepared from HeLa (Lane 1), Ltk⁻ (Lane 2) and He1 (Lane 3) poly A+ RNA. The primers used were from the N-terminal and C-terminal coding regions of ICAM-1 having the sequence ggaattcATGGCTCCCAGCAGCCCCCG-GCCC SEQ ID NO: 1 and ggaattcTCAGGGAGGCGTG-GCTTGTGTGTT SEQ ID NO: 2. Upper case denotes ICAM-1 sequence, lower case restriction site linkers. Lanes 1 and 2, 72 hour exposure, Lane 3, 90 minute exposure.
Figure 5:
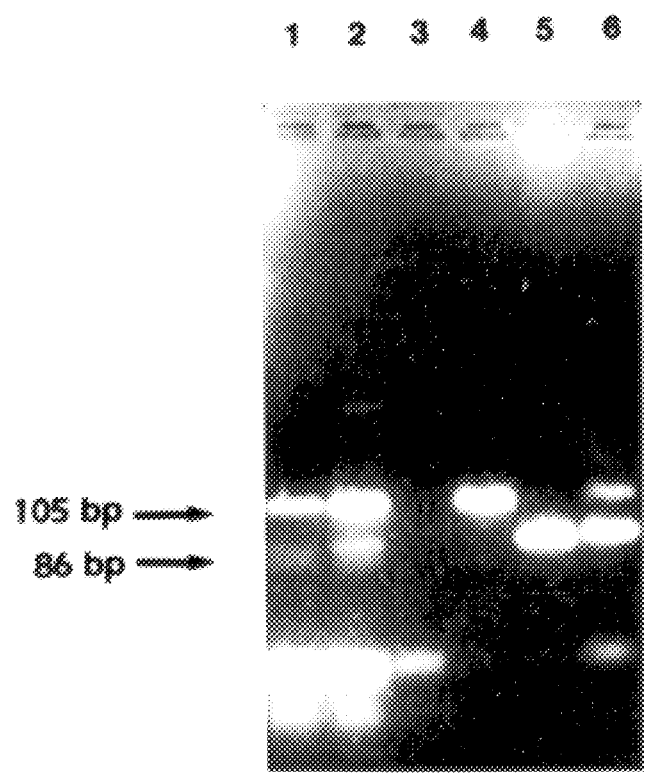
FIG. 5 is a gel showing the detection of the ICAM-1 and sICAM-1 mRNAs in HeLa and He1 cells. PCR amplification was performed on 100 ng single stranded CDNA using the primers PCR 5.4 (CTTGAGGGCACCTACCTCTGTCGG SEQ ID NO: 3) and PCR 3.4 (AGTGATGATGACAATCTCATACCG SEQ ID NO: 1). Extensions were performed at 72 C for 25 cycles and one tenth of the product was analysed on a 1% agarose/3% NuSieve gel. Lane 1, HeLa cDNA; lane 2, He1 cDNA; lane 3, LTK⁻ cDNA; lane 4, ICAM-1 phage control; lane 5, sICAM-1 phage control; lane 6, ICAM-1+sICAM-1 phage control. Specific amplification products of 105 bp and 86 bp are indicated by the arrows.
Figure 6:
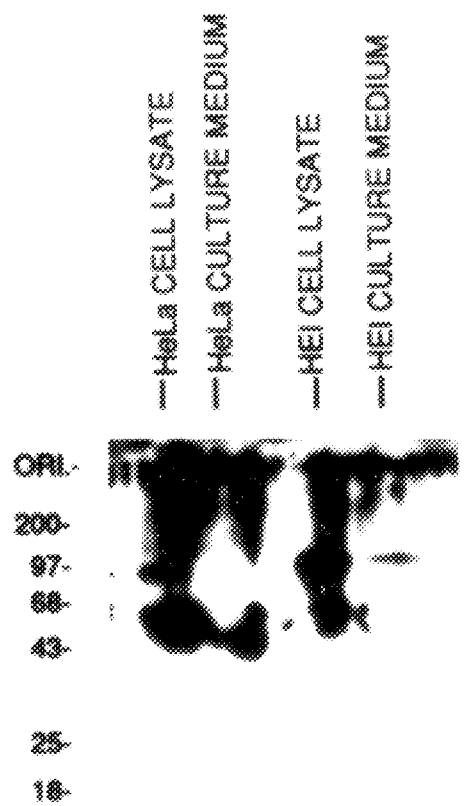
FIG. 6 is a Western blot showing the synthesis of a soluble form of ICAM-1 protein by HeLa and HE1 cells. It demonstrates the existence of a protein species in the culture supernatant of HeLa and HE1 cells related to ICAM-1. Equivalent aliquots of cell lysates and culture supernatants were separated by SDS-PAGE, blotted onto nitrocellulose, and probed with a rabbit polyclonal antisera to ICAM-1 followed by $^{125}$I protein A; a species migrating close to the position of membrane-bound ICAM-1 is seen in both HeLa and He1 culture supernatants.

A randomly primed cDNA library was constructed in lambda GT11 from He1 poly A+ by Clontech Laboratories, Palo Alto, Calif. The library was screened with two 47 mer oligonucleotide probes from the middle of the ICAM-1 coding sequence. A positive clone designated 19.1–3 was isolated which had an insert of 1.5 kb; a second cDNA clone designated 4.5 which has an insert of 1.25 kb was isolated; and an additional cDNA clone pHRR-3 was obtained by subcloning the products of PCR amplification into Bluescript utilizing the Perkin-Elmer/Cetus DNA Amplification System, Perkin Elmer, Wellesley Mass., as shown in FIG. 4C, lane 3. These clones showed a significant difference from the published ICAM-1 sequence. They all contain a deletion of 19 base pairs from nucleotide 1465 to 1483 according to the numbering of Staunton et al, supra. In order to demonstrate directly that the s-ICAM mRNA is present in He1 cells and HeLa cels, a PCR experiment was performed using primers which flank the 19 bp region which is absent from the S-ICAM mRNA (FIG. 8). Using these primers the product from the ICAM-1 mRNA is 105 bp while the s-ICAM-1 product is 19 bp shorter i.e. 86 bp. This experiment shows that both HEI cells and HeLa cells contain both forms of the ICAM-1 MRNA while the control L-cells do not. A synthetic oligonucleotide designated PCR3.2 having the following sequence:

ggaattcTCACTCATACCGGGGGGAGAGCACATT SEQ ID NO: 7 was used to distinguish between cDNA clones containing the 19 bp deletion from clones not containing the 19 bp deletion. The synthetic oligonucleotide does not bind to cDNA clones which contain the 19 bp deletion. In addition, partial sequence of the cDNA 19.1–3 and PHRR-3 confirmed the 19 bp deletion. This data indicates that there are at least two different and distinct ICAM-1 species in He1 cells. The insoluble ICAM-1 of the prior art and a novel soluble form as described in the present invention.

The sequences of the deleted (sICAM-1) and the nondeleted (ICAM-1) forms of the Intercellular Adhesion Molecule-1 mRNA represented by the cDNA clones are shown in FIG. 2. The sequence at the point of deletion is AGGT consistent with an RNA splice junction. The removal of 19 bases from the mRNA shifts the reading frame and causes the two polypeptide sequences to diverge at amino acid residue 443. The deleted form (sICAM-1) contains an additional 11 residues followed by an in-frame termination codon. This molecule thus consists of 453 amino acids as compared to 505 amino acids for the nondeleted form. Beginning with the N-terminus of ICAM-1, sICAM-1 has 442 amino acids in common with ICAM-1. The deleted form (sICAM-1) contains a unique 11 amino acid C-terminus but lacks the membrane spanning (24 amino acids) and cytoplasmic tail 28 amino acids) domains of ICAM-1, as shown in FIG. 3.

ICAM-1 cDNA Clones

A plurality of methods may be used to clone genes. One method is to use two partially overlapping 47mer oligonucleotide probes. These two probes termed oligonucleotide ICAM-1 and oligonucleotide ICAM-3 were synthesized from the published ICAM-1 sequence. The ICAM-1 oligonucleotide was labeled to high specific activity and hybridized to a Southern blot under high stringency conditions. As shown in FIG. 4A, a single band of 4.4 kb was detected in HeLa, He1 and two primary HRR transfectant cell lines and was absent from Ltk- cells. This result confirms that the HRR transfectants contain the human ICAM-1 gene. The size of the fragment agrees with Simmons et al but differs from Staunton et al probably reflecting a restriction site polymorphism.

The ICAM-1 oligonucleotide was used to probe a Northern blot of poly A+ RNA from the same cell lines. As shown in FIG. 4B, an mRNA of 3.3 kb was detected in HeLa, HE1, and primary transfectant cell lines but was absent from Ltk⁻ cells. The signal in He1 cells was many times stronger than the other cell lines indicating a much higher level of mRNA in HE1 cells. This is in agreement with the higher level of HRR (ICAM-1) expression in He1 cells. A second 2.4 kb RNA was also detected in He1 cells. These data confirm that the human ICAM-1 mRNA is expressed in HRR transfectants. See FIG. 4B.

The human ICAM-1 gene was isolated from the HE1 transfectant using polymerase chain reaction (PCR) amplification utilizing the Perkin-Elmer/Seats DNA Amplification System, Perkin Elmer, Wellesley Mass. PCR amplification was performed on single stranded cDNA made from HeLa, Ltd⁻ and He1 RNA. Primers were made from the 5' and 3' coding regions of the published ICAM-1 sequence. ICAM-1 specific amplification products were detected by hybridization of a Southern blot of the PCR reactions using the ICAM-1 oligonucleotide. As shown in FIG. 4C, a single band of approximately 1600 bp which matches the predicted size was amplified from HeLa cells and He1 cells but was absent from Ltk⁻ cells. The amplification product was cloned into Bluescript (Strategene, San Diego, Calif.) and two independent clones designated PHRR1 and PHRR2 were obtained. The complete sequence of PHRR2 showed 100% identity with the published ICAM-1 coding sequence with the exception of a single A to G change previously described.

A lambda GT11 library made from randomly primed HEI cDNA was screened with the ICAM-1 and ICAM-3 probes and eight positive clones were isolated. Six clones as shown in FIG. 7 were selected for further study and were analyzed by partial DNA sequencing. A total of approximately 1000 nucleotides of sequence derived from these clones showed identity with the ICAM-1 sequence.

Purification and Isolation of Soluble Protein

HeLa and He1 cells are grown under standard conditions in DMEM (Dulbecco's Modified Essential Media) with 10% Fetal Bovine Serum. Conditioned media from these cells is harvested and centrifuged or filtered to remove cells or cellular debris. The cell-membrane bound ICAM-1 is not present in the supernatant. This media is then absorbed to a monoclonal antibody-sepharose resin (the monoclonal antibody c78.4A being an example) in which the monoclonal antibody is directed to ICAM-1 or sICAM-1 and the unabsorbed proteins are washed from the resin with a physiological saline buffer, such as phosphate-buffered saline. The bound sICAM-1 is then eluted under conditions that preserve the native conformation of the protein, as described in copending application Ser. No. 262428 filed Oct. 25, 1988 now abandoned. The sICAM-1 may be further purified by lectin affinity chromatography, ion exchange chromatography, or gel filtration.

mRNA transcribed in vitro from cDNA encoding sICAM in the Bluescript vector (Strategene) was translated in vitro. In the absence of microsomal membranes, an unglycosylated protein with an apparent MW of 52,000 daltons was obtained; in the presence of microsomal membranes, a glycosylated species of 72,400 daltons was obtained which was sequestered within the microsomal membrane, indicating that the sICAM polypeptide is correctly translocated, processed, and glycosylated by the microsomal membranes.

cDNA's encoding tmICAM and sICAM in the CDM8 vector (Seed, B. and Aruffo, A. PNAS 84:3365 (1987) were transfected into COS cells and mouse L cells using the DEAE-dextran technique. AT 72 hra the cells were analyzed by two methods: (1) FACS analysis with anti-ICAM Mab (c78.4) for cell membrane expression of ICAM species and (2) metabolic labeling followed by immunoabsorption with anti-ICAM Mab of cell supernatants and cell lysates. The results from the metabolic labelling indicated intracellular accumulation of a 68,000 dalton species in sICAM-transfected cells but no detectable secretion of sICAM into the supernatant. These data are consistent with sICAM being secreted through the "Regulated" secretory pathway (R. B. Kelly, Science 230:25 (1985)).

Antibody probes specific for sICAM and for ICAM-1 were prepared. The synthetic peptides S-PEP,

P P G M R L S S S L W (C) SEQ ID NO: 8 derived from a unique 11 amino acid sequence at the C-terminus of sICAM, and P002, derived from the C-terminus of ICAM-1,

G T P M K P N T Q A T P P (C) SEQ ID NO: 9 was made and purified; the C-terminal C residues in parentheses were added to facilitate coupling of the peptides to protein carriers. The synthetic peptide was coupled to KLH (Keyhole Limpet Hemocyanin) by standard procedures and the conjugate injected into rabbits to produce anti-peptide antisera were shown to specifically bind to their respective peptide immunogens.

What is claimed is:

1. Purified and isolated soluble intercellular adhesion molecule-1 having the amino acid sequence as shown in SEQ ID NO: 11.

2. Purified and isolated soluble intercellular adhesion molecule-1 obtained from cells selected from the group consisting of a) cells containing genomic DNA coding for intercellular adhesion molecule-1, which DNA is transcribed into alternatively spliced mRNA which is translated into soluble intercellular adhesion molecule-1, and b) cells containing DNA coding for soluble intercellular adhesion molecule-1, wherein said soluble intercellular adhesion molecule-1 is characterized by being soluble in the absence of detergent and by being the translation product of the mRNA sequence corresponding to the cDNA sequence shown in SEQ ID NO.10.

3. A pharmaceutical composition comprising purified soluble intercellular adhesion molecule-1 having the amino acid sequence shown in SEQ ID NO: 11, in conjunction with a pharmaceutically acceptable carrier.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: no ( i x ) FEATURE:
    ( A ) NAME/KEY: PCR 5.1 (5'PCR primer)
    ( B ) LOCATION: 5'end of ICAM-1 coding sequence
    ( D ) OTHER INFORMATION: bp 1 = G; bp 2-7 = EcoRI
        site; bp 8- 31 = 24 bases coding for the first
        eight amino acid residues of hICAM-1

( x ) PUBLICATION INFORMATION:
    ( A ) AUTHORS: Greve, J.M., G. Davis, A.M. Meyer,
        C.P. Forte, S.C. Yost, C.W. Marlor, M.E.
        Kamarck, and A. McClelland
    ( B ) TITLE: The Major Human Rhinovirus Receptor is
        ICAM-1
    ( C ) JOURNAL: Cell
    ( D ) VOLUME: 56
    ( F ) PAGES: 839-847
    ( G ) DATE: March 10, 1989
    ( K ) RELEVANT RESIDUES IN SEQ ID NO:1: FROM 1 TO
        31

( x i ) SEQUENCE DESCRIPTION: SEQ ID NO:1:

```
GGAATTC ATG GCT CCC AGC AGC CCC CGG CCC                    31
        Met Ala Pro Ser Ser Pro Arg Pro
                         5
```

( 2 ) INFORMATION FOR SEQ ID NO:2:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: yes ( i x ) FEATURE:
        ( A ) NAME/KEY: PCR 3.1 (3'PCR primer)
        ( B ) LOCATION: 3'end of ICAM-1 coding sequence
        ( D ) OTHER INFORMATION: base 1 =G; base 2-7 =
            EcoRI site; base 8-31 = 24 bases
            complementary to nucleic acid sequence coding
            for last 8 amino acid residues of hICAM-1

( x ) PUBLICATION INFORMATION:
        ( A ) AUTHORS: Greve, J.M., G. Davis, A.M. Meyer,
            C.P. Forte, S.C. Yost, C.W. Marlor, M.E.
            Kamarck, and A. McClelland
        ( B ) TITLE: The Major Human Rhinovirus Receptor is
            ICAM-1
        ( C ) JOURNAL: Cell
        ( D ) VOLUME: 56
        ( F ) PAGES: 839-847
        ( G ) DATE: March 10, 1989
        ( K ) RELEVANT RESIDUES IN SEQ ID NO:2: FROM 1 TO
            31

( x i ) SEQUENCE DESCRIPTION: SEQ ID NO:2:

```
GGAATTCTCA GGGAGGCGTG GCTTGTGTGT T                         31
```

( 2 ) INFORMATION FOR SEQ ID NO:3:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: no ( i x ) FEATURE:
    ( A ) NAME/KEY: PCR 5.4 (5'PCR primer)
    ( B ) LOCATION: nucleotides 1351 to 1374 of sICAM ( x i ) SEQUENCE DESCRIPTION: SEQ ID NO:3:

```
CTT  GAG  GGC  ACC  TAC  CTC  TGT  CGG                                    24
Leu  Glu  Gly  Thr  Tyr  Leu  Cys  Arg
               5
```

( 2 ) INFORMATION FOR SEQ ID NO:4:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: yes ( i x ) FEATURE:
        ( A ) NAME/KEY: 3'PCR primer
        ( B ) LOCATION: complementary to nucleotides 1432 -
            1455 of sICAM ( x i ) SEQUENCE DESCRIPTION: SEQ ID NO:4:

```
AGTGATGATG  ACAATCTCAT  ACCG                                              24
```

( 2 ) INFORMATION FOR SEQ ID NO:5:

( i ) SEQUENCE CHARACTERISTICS:
        ( A ) LENGTH: 47 bases
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: yes ( i x ) FEATURE:
        ( A ) NAME/KEY: ICAM1 probe
        ( B ) LOCATION: complementary to nucleotides 565 to
            611 of ICAM- 1

( x ) PUBLICATION INFORMATION:
        ( A ) AUTHORS: Greve, J.M., G. Davis, A.M. Meyer,
            C.P. Forte, S.C. Yost, C.W. Marlor, M.E.
            Kamarck, and A. McClelland
        ( B ) TITLE: The Major Human Rhinovirus Receptor is
            ICAM-1
        ( C ) JOURNAL: Cell
        ( D ) VOLUME: 56
        ( F ) PAGES: 839-847
        ( G ) DATE: March 10, 1989
        ( K ) RELEVANT RESIDUES IN SEQ ID NO:5: FROM 1 TO
            47

( x i ) SEQUENCE DESCRIPTION: SEQ ID NO:5:

```
GAGGTGTTCT  CAAACAGCTC  CAGCCCTTGG  GGCCGCAGGT  CCAGTTC                    47
```

( 2 ) INFORMATION FOR SEQ ID NO:6:

( i ) SEQUENCE CHARACTERISTICS:
        ( A ) LENGTH: 47 bases
        ( B ) TYPE: nucleic acid (C) STRANDEDNESS: single
(D) TOPOLOGY: linear (i i) MOLECULE TYPE: other nucleic acid (i i i) HYPOTHETICAL: no (i v) ANTI-SENSE: yes (i x) FEATURE:
(A) NAME/KEY: ICAM3 probe
(B) LOCATION: complementary to nucleotides 602 to
648 of human ICAM (x) PUBLICATION INFORMATION:
(A) AUTHORS: Greve, J.M., G. Davis, A.M. Meyer,
C.P. Forte, S.C. Yost, C.W. Marlor, M.E.
Kamarck, and A. McClelland
(B) TITLE: The Major Human Rhinovirus Receptor is
ICAM-1
(C) JOURNAL: Cell
(D) VOLUME: 56
(F) PAGES: 839-847
(G) DATE: March 10, 1989
(K) RELEVANT RESIDUES IN SEQ ID NO:6: FROM 1 TO
47

(x i) SEQUENCE DESCRIPTION: SEQ ID NO:6:

CGTTGGCAGG ACAAAGGTCT GGAGCTGGTA GGGGGCCGAG GTGTTCT    47

(2) INFORMATION FOR SEQ ID NO:7:

(i) SEQUENCE CHARACTERISTICS:
(A) LENGTH: 34 bases
(B) TYPE: nucleic acid
(C) STRANDEDNESS: single
(D) TOPOLOGY: linear (i i) MOLECULE TYPE: other nucleic acid (i i i) HYPOTHETICAL: no (i v) ANTI-SENSE: yes (i x) FEATURE:
(A) NAME/KEY: PCR 3.2 antisense
(D) OTHER INFORMATION: base 1 =G; bases 2-7 =
EcoR1 site; bases 8-10 = complementary to a
stop codon; bases 11-34 = 24 bases
complementary to nucleotides 1474-1497 of
ICAM-1, nucleotide 1 being the ATG (x i) SEQUENCE DESCRIPTION: SEQ ID NO:7:

GGAATTCTCA CTCATACCGG GGGGAGAGCA CATT    34

(2) INFORMATION FOR SEQ ID NO:8:

(i) SEQUENCE CHARACTERISTICS:
(A) LENGTH: 12 amino acid residues
(B) TYPE: amino acid
(D) TOPOLOGY: linear (i i) MOLECULE TYPE:
(A) DESCRIPTION: peptide (i i i) HYPOTHETICAL: no (v) FRAGMENT TYPE: modified C-terminal fragment (i x) FEATURE:
(A) NAME/KEY: modified sICAM fragment
(B) LOCATION: C-terminus of sICAM
(D) OTHER INFORMATION: first 11 amino acids
correspond to C-terminus of sICAM; last
residue (Cys) added to faciliate coupling ( x i ) SEQUENCE DESCRIPTION: SEQ ID NO:8:

| Pro | Pro | Gly | Met | Arg | Leu | Ser | Ser | Ser | Leu | Trp | Cys |
|-----|-----|-----|-----|-----|-----|-----|-----|-----|-----|-----|-----|
|     |     |     |     | 5   |     |     |     |     | 10  |     |     |

( 2 ) INFORMATION FOR SEQ ID NO:9:

( i ) SEQUENCE CHARACTERISTICS:
        ( A ) LENGTH: 14 amino acid residues
        ( B ) TYPE: amino acid
        ( D ) TOPOLOGY: linear ( i i ) MOLECULE TYPE:
        ( A ) DESCRIPTION: peptide ( i i i ) HYPOTHETICAL: no ( v ) FRAGMENT TYPE: C-terminal fragment ( i x ) FEATURE:
        ( A ) NAME/KEY: modified ICAM fragment
        ( B ) LOCATION: C-terminus
        ( D ) OTHER INFORMATION: first 11 amino acid
            residues correspond to the C-terminus of
            ICAM; last residue (Cys) added to faciliate
            coupling ( x i ) SEQUENCE DESCRIPTION: SEQ ID NO:9:

| Gly | Thr | Pro | Met | Lys | Pro | Asn | Thr | Gln | Ala | Thr | Pro | Pro | Cys | 14 |
|-----|-----|-----|-----|-----|-----|-----|-----|-----|-----|-----|-----|-----|-----|----|
|     |     |     |     | 5   |     |     |     |     | 10  |     |     |     |     |    |

( 2 ) INFORMATION FOR SEQ ID NO:10:

( i ) SEQUENCE CHARACTERISTICS:
        ( A ) LENGTH: 1443 bases
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: human
        ( G ) CELL TYPE: epithelial
        ( H ) CELL LINE: HeLa ( v i i ) IMMEDIATE SOURCE:
        ( A ) LIBRARY: cDNA library ( i x ) FEATURE:
        ( A ) NAME/KEY: human sICAM cDNA to mRNA sequence
        ( B ) LOCATION: nucleotides 1 to 1435 numbered
            beginning at ATG coding for first Met of
            human sICAM protein ( x i ) SEQUENCE DESCRIPTION: SEQ ID NO:10:

| ATG | GCT | CCC | AGC | AGC | CCC | CGG | CCC | GCG | CTG | CCC | GCA | CTC | CTG | GTC | 45 |
|-----|-----|-----|-----|-----|-----|-----|-----|-----|-----|-----|-----|-----|-----|-----|----|
| Met | Ala | Pro | Ser | Ser | Pro | Arg | Pro | Ala | Leu | Pro | Ala | Leu | Leu | Val |    |
|     |     |     |     | 5   |     |     |     |     | 10  |     |     |     |     | 15  |    |
| CTG | CTC | GGG | GCT | CTG | TTC | CCA | GGA | CCT | GGC | AAT | GCC | CAG | ACA | TCT | 90 |
| Leu | Leu | Gly | Ala | Leu | Phe | Pro | Gly | Pro | Gly | Asn | Ala | Gln | Thr | Ser |    |
|     |     |     |     | 20  |     |     |     |     | 25  |     |     |     |     | 30  |    |
| GTG | TCC | CCC | TCA | AAA | GTC | ATC | CTG | CCC | CGG | GGA | GGC | TCC | GTG | CTG | 135 |
| Val | Ser | Pro | Ser | Lys | Val | Ile | Leu | Pro | Arg | Gly | Gly | Ser | Val | Leu |    |
|     |     |     |     | 35  |     |     |     |     | 40  |     |     |     |     | 45  |    |
| GTG | ACA | TGC | AGC | ACC | TCC | TGT | GAC | CAG | CCC | AAG | TTG | TTG | GGC | ATA | 180 |
| Val | Thr | Cys | Ser | Thr | Ser | Cys | Asp | Gln | Pro | Lys | Leu | Leu | Gly | Ile |    |
|     |     |     |     | 50  |     |     |     |     | 55  |     |     |     |     | 60  |    |

```
GAG  ACC  CCG  TTG  CCT  AAA  AAG  GAG  TTG  CTC  CTG  CCT  GGG  AAC  AAC         225
Glu  Thr  Pro  Leu  Pro  Lys  Lys  Glu  Leu  Leu  Leu  Pro  Gly  Asn  Asn
               65                  70                       75

CGG  AAG  GTG  TAT  GAA  CTG  AGC  AAT  GTG  CAA  GAA  GAT  AGC  CAA  CCA         270
Arg  Lys  Val  Tyr  Glu  Leu  Ser  Asn  Val  Gln  Glu  Asp  Ser  Gln  Pro
                    80                  85                            90

ATG  TGC  TAT  TCA  AAC  TGC  CCT  GAT  GGG  CAG  TCA  ACA  GCT  AAA  ACC         315
Met  Cys  Tyr  Ser  Asn  Cys  Pro  Asp  Gly  Gln  Ser  Thr  Ala  Lys  Thr
                    95                  100                          105

TTC  CTC  ACC  GTG  TAC  TGG  ACT  CCA  GAA  CGG  GTG  GAA  CTG  GCA  CCC         360
Phe  Leu  Thr  Val  Tyr  Trp  Thr  Pro  Glu  Arg  Val  Glu  Leu  Ala  Pro
                    110                 115                          120

CTC  CCC  TCT  TGG  CAG  CCA  GTG  GGC  AAG  AAC  CTT  ACC  CTA  CGC  TGC         405
Leu  Pro  Ser  Trp  Gln  Pro  Val  Gly  Lys  Asn  Leu  Thr  Leu  Arg  Cys
                    125                 130                          135

CAG  GTG  GAG  GGT  GGG  GCA  CCC  CGG  GCC  AAC  CTC  ACC  GTG  GTG  CTG         450
Gln  Val  Glu  Gly  Gly  Ala  Pro  Arg  Ala  Asn  Leu  Thr  Val  Val  Leu
                    140                 145                          150

CTC  CGT  GGG  GAG  AAG  GAG  CTG  AAA  CGG  GAG  CCA  GCT  GTG  GGG  GAG         495
Leu  Arg  Gly  Glu  Lys  Glu  Leu  Lys  Arg  Glu  Pro  Ala  Val  Gly  Glu
                    155                 160                          165

CCC  GCT  GAG  GTC  ACG  ACC  ACG  GTG  CTG  GTG  AGG  AGA  GAT  CAC  CAT         540
Pro  Ala  Glu  Val  Thr  Thr  Thr  Val  Leu  Val  Arg  Arg  Asp  His  His
                    170                 175                          180

GGA  GCC  AAT  TTC  TCG  TGC  CGC  ACT  GAA  CTG  GAC  CTG  CGG  CCC  CAA         585
Gly  Ala  Asn  Phe  Ser  Cys  Arg  Thr  Glu  Leu  Asp  Leu  Arg  Pro  Gln
                    185                 190                          195

GGG  CTG  GAG  CTG  TTT  GAG  AAC  ACC  TCG  GCC  CCC  TAC  CAG  CTC  CAG         630
Gly  Leu  Glu  Leu  Phe  Glu  Asn  Thr  Ser  Ala  Pro  Tyr  Gln  Leu  Gln
                    200                 205                          210

ACC  TTT  GTC  CTG  CCA  GCG  ACT  CCC  CCA  CAA  CTT  GTC  AGC  CCC  CGG         675
Thr  Phe  Val  Leu  Pro  Ala  Thr  Pro  Pro  Gln  Leu  Val  Ser  Pro  Arg
                    215                 220                          225

GTC  CTA  GAG  GTG  GAC  ACG  CAG  GGG  ACC  GTG  GTC  TGT  TCC  CTG  GAC         720
Val  Leu  Glu  Val  Asp  Thr  Gln  Gly  Thr  Val  Val  Cys  Ser  Leu  Asp
                    230                 235                          240

GGG  CTG  TTC  CCA  GTC  TCG  GAG  GCC  CAG  GTC  CAC  CTG  GCA  CTG  GGG         765
Gly  Leu  Phe  Pro  Val  Ser  Glu  Ala  Gln  Val  His  Leu  Ala  Leu  Gly
                    245                 250                          255

GAC  CAG  AGG  TTG  AAC  CCC  ACA  GTC  ACC  TAT  GGC  AAC  GAC  TCC  TTC         810
Asp  Gln  Arg  Leu  Asn  Pro  Thr  Val  Thr  Tyr  Gly  Asn  Asp  Ser  Phe
                    260                 265                          270

TCG  GCC  AAG  GCC  TCA  GTC  AGT  GTG  ACC  GCA  GAG  GAC  GAG  GGC  ACC         855
Ser  Ala  Lys  Ala  Ser  Val  Ser  Val  Thr  Ala  Glu  Asp  Glu  Gly  Thr
                    275                 280                          285

CAG  CGG  CTG  ACG  TGT  GCA  GTA  ATA  CTG  GGG  AAC  CAG  AGC  CAG  GAG         900
Gln  Arg  Leu  Thr  Cys  Ala  Val  Ile  Leu  Gly  Asn  Gln  Ser  Gln  Glu
                    290                 295                          300

ACA  CTG  CAG  ACA  GTG  ACC  ATC  TAC  AGC  TTT  CCG  GCG  CCC  AAC  GTG         945
Thr  Leu  Gln  Thr  Val  Thr  Ile  Tyr  Ser  Phe  Pro  Ala  Pro  Asn  Val
                    305                 310                          315

ATT  CTG  ACG  AAG  CCA  GAG  GTC  TCA  GAA  GGG  ACC  GAG  GTG  ACA  GTG         990
Ile  Leu  Thr  Lys  Pro  Glu  Val  Ser  Glu  Gly  Thr  Glu  Val  Thr  Val
                    320                 325                          330

AAG  TGT  GAG  GCC  CAC  CCT  AGA  GCC  AAG  GTG  ACG  CTG  AAT  GGG  GTT        1035
Lys  Cys  Glu  Ala  His  Pro  Arg  Ala  Lys  Val  Thr  Leu  Asn  Gly  Val
                    335                 340                          345

CCA  GCC  CAG  CCA  CTG  GGC  CCG  AGG  GCC  CAG  CTC  CTG  CTG  AAG  GCC        1080
Pro  Ala  Gln  Pro  Leu  Gly  Pro  Arg  Ala  Gln  Leu  Leu  Leu  Lys  Ala
                    350                 355                          360
```

| | | | | | | | | | | | | | | |
|---|---|---|---|---|---|---|---|---|---|---|---|---|---|---|
| ACC | CCA | GAG | GAC | AAC | GGG | CGC | AGC | TTC | TCC | TGC | TCT | GCA | ACC | CTG | 1125
| Thr | Pro | Glu | Asp | Asn | Gly | Arg | Ser | Phe | Ser | Cys | Ser | Ala | Thr | Leu |
| | | | | 365 | | | | 370 | | | | | 375 | |
| GAG | GTG | GCC | GGC | CAG | CTT | ATA | CAC | AAG | AAC | CAG | ACC | CGG | GAG | CTT | 1170
| Glu | Val | Ala | Gly | Gln | Leu | Ile | His | Lys | Asn | Gln | Thr | Arg | Glu | Leu |
| | | | | 380 | | | | 385 | | | | | 390 | |
| CGT | GTC | CTG | TAT | GGC | CCC | CGA | CTG | GAC | GAG | AGG | GAT | TGT | CCG | GGA | 1215
| Arg | Val | Leu | Tyr | Gly | Pro | Arg | Leu | Asp | Glu | Arg | Glu | Cys | Pro | Gly |
| | | | | 395 | | | | 400 | | | | | 405 | |
| AAC | TGG | ACG | TGG | CCA | GAA | AAT | TCC | CAG | CAG | ACT | CCA | ATG | TGC | CAG | 1260
| Asn | Trp | Thr | Trp | Pro | Glu | Asn | Ser | Gln | Gln | Thr | Pro | Met | Cys | Gln |
| | | | | 410 | | | | 415 | | | | | 420 | |
| GCT | TGG | GGG | AAC | CCA | TTG | CCC | GAG | CTC | AAG | TGT | CTA | AAG | GAT | GGC | 1305
| Ala | Trp | Gly | Asn | Pro | Leu | Pro | Glu | Leu | Lys | Cys | Leu | Lys | Asp | Gly |
| | | | | 425 | | | | 430 | | | | | 435 | |
| ACT | TTC | CCA | CTG | CCC | ATC | GGG | GAA | TCA | GTG | ACT | GTC | ACT | CGA | GAT | 1350
| Thr | Phe | Pro | Leu | Pro | Ile | Gly | Glu | Ser | Val | Thr | Val | Thr | Arg | Asp |
| | | | | 440 | | | | 445 | | | | | 450 | |
| CTT | GAG | GGC | ACC | TAC | CTC | TGT | CGG | GCC | AGG | AGC | ACT | CAA | GGG | GAG | 1395
| Leu | Glu | Gly | Thr | Tyr | Leu | Cys | Arg | Ala | Arg | Ser | Thr | Gln | Gly | Glu |
| | | | | 455 | | | | 460 | | | | | 465 | |
| GTC | ACC | CGC | AAG | CCC | CCC | GGT | ATG | AGA | TTG | TCA | TCA | TCA | CTG | TGG | 1440
| Val | Thr | Arg | Lys | Pro | Pro | Gly | Met | Arg | Leu | Ser | Ser | Ser | Leu | Trp |
| | | | | 470 | | | | 475 | | | | | 480 | |
| TAG | | | | | | | | | | | | | | | 1443

( 2 ) INFORMATION FOR SEQ ID NO:11:

( i ) SEQUENCE CHARACTERISTICS:
        ( A ) LENGTH: 480 amino acid residues
        ( B ) TYPE: amino acid
        ( D ) TOPOLOGY: linear ( i i ) MOLECULE TYPE:
        ( A ) DESCRIPTION: protein ( i i i ) HYPOTHETICAL: no ( v i ) ORIGINAL SOURCE:
        ( A ) ORGANISM: human
        ( B ) CELL TYPE: epithelial
        ( C ) CELL LINE: HeLa cells ( i x ) FEATURE:
        ( A ) NAME/KEY: sICAM-1
        ( D ) OTHER INFORMATION: amino acid sequence
            identical to ICAM-1 protein sequence except
            for residue 442, which is Lys rather than
            Glu, and residues 443-453, which is novel
            sequence due to alternative splicing ( x i ) SEQUENCE DESCRIPTION: SEQ ID NO:11:

| | | | | | | | | | | | | | | |
|---|---|---|---|---|---|---|---|---|---|---|---|---|---|---|
| Met | Ala | Pro | Ser | Ser | Pro | Arg | Pro | Ala | Leu | Pro | Ala | Leu | Leu | Val |
| | | | | 5 | | | | 10 | | | | | 15 | |
| Leu | Leu | Gly | Ala | Leu | Phe | Pro | Gly | Pro | Gly | Asn | Ala | Gln | Thr | Ser |
| | | | | 20 | | | | 25 | | | | | 30 | |
| Val | Ser | Pro | Ser | Lys | Val | Ile | Leu | Pro | Arg | Gly | Gly | Ser | Val | Leu |
| | | | | 35 | | | | 40 | | | | | 45 | |
| Val | Thr | Cys | Ser | Thr | Ser | Cys | Asp | Gln | Pro | Lys | Leu | Leu | Gly | Ile |
| | | | | 50 | | | | 55 | | | | | 60 | |
| Glu | Thr | Pro | Leu | Pro | Lys | Lys | Glu | Leu | Leu | Leu | Pro | Gly | Asn | Asn |
| | | | | 65 | | | | 70 | | | | | 75 | |
| Arg | Lys | Val | Tyr | Glu | Leu | Ser | Asn | Val | Gln | Glu | Asp | Ser | Gln | Pro |
| | | | | 80 | | | | 85 | | | | | 90 | |

```
Met Cys Tyr Ser Asn Cys Pro Asp Gly Gln Ser Thr Ala Lys Thr
                 95                  100                 105

Phe Leu Thr Val Tyr Trp Thr Pro Glu Arg Val Glu Leu Ala Pro
                110                  115                 120

Leu Pro Ser Trp Gln Pro Val Gly Lys Asn Leu Thr Leu Arg Cys
                125                  130                 135

Gln Val Glu Gly Gly Ala Pro Arg Ala Asn Leu Thr Val Val Leu
                140                  145                 150

Leu Arg Gly Glu Lys Glu Leu Lys Arg Glu Pro Ala Val Gly Glu
                155                  160                 165

Pro Ala Glu Val Thr Thr Thr Val Leu Val Arg Arg Asp His His
                170                  175                 180

Gly Ala Asn Phe Ser Cys Arg Thr Glu Leu Asp Leu Arg Pro Gln
                185                  190                 195

Gly Leu Glu Leu Phe Glu Asn Thr Ser Ala Pro Tyr Gln Leu Gln
                200                  205                 210

Thr Phe Val Leu Pro Ala Thr Pro Pro Gln Leu Val Ser Pro Arg
                215                  220                 225

Val Leu Glu Val Asp Thr Gln Gly Thr Val Val Cys Ser Leu Asp
                230                  235                 240

Gly Leu Phe Pro Val Ser Glu Ala Gln Val His Leu Ala Leu Gly
                245                  250                 255

Asp Gln Arg Leu Asn Pro Thr Val Thr Tyr Gly Asn Asp Ser Phe
                260                  265                 270

Ser Ala Lys Ala Ser Val Ser Val Thr Ala Glu Asp Glu Gly Thr
                275                  280                 285

Gln Arg Leu Thr Cys Ala Val Ile Leu Gly Asn Gln Ser Gln Glu
                290                  295                 300

Thr Leu Gln Thr Val Thr Ile Tyr Ser Phe Pro Ala Pro Asn Val
                305                  310                 315

Ile Leu Thr Lys Pro Glu Val Ser Glu Gly Thr Glu Val Thr Val
                320                  325                 330

Lys Cys Glu Ala His Pro Arg Ala Lys Val Thr Leu Asn Gly Val
                335                  340                 345

Pro Ala Gln Pro Leu Gly Pro Arg Ala Gln Leu Leu Leu Lys Ala
                350                  355                 360

Thr Pro Glu Asp Asn Gly Arg Ser Phe Ser Cys Ser Ala Thr Leu
                365                  370                 375

Glu Val Ala Gly Gln Leu Ile His Lys Asn Gln Thr Arg Glu Leu
                380                  385                 390

Arg Val Leu Tyr Gly Pro Arg Leu Asp Glu Arg Glu Cys Pro Gly
                395                  400                 405

Asn Trp Thr Trp Pro Glu Asn Ser Gln Gln Thr Pro Met Cys Gln
                410                  415                 420

Ala Trp Gly Asn Pro Leu Pro Glu Leu Lys Cys Leu Lys Asp Gly
                425                  430                 435

Thr Phe Pro Leu Pro Ile Gly Glu Ser Val Thr Val Thr Arg Asp
                440                  445                 450

Leu Glu Gly Thr Tyr Leu Cys Arg Ala Arg Ser Thr Gln Gly Glu
                455                  460                 465

Val Thr Arg Lys Pro Pro Gly Met Arg Leu Ser Ser Ser Leu Trp
                470                  475                 480
```

( 2 ) INFORMATION FOR SEQ ID NO:12:

(i) SEQUENCE CHARACTERISTICS:
    (A) LENGTH: 240 bases
    (B) TYPE: nucleic acid
    (C) STRANDEDNESS: single
    (D) TOPOLOGY: linear (ii) MOLECULE TYPE: cDNA to mRNA (iii) HYPOTHETICAL: no (iv) ANTI-SENSE: no (vi) ORIGINAL SOURCE:
    (A) ORGANISM: human
    (G) CELL TYPE: epithelial
    (H) CELL LINE: HeLa (vii) IMMEDIATE SOURCE:
    (A) LIBRARY: cDNA library (ix) FEATURE:
    (A) NAME/KEY: partial human ICAM cDNA to mRNA sequence
    (B) LOCATION: nucleotides 1384 to 1623 numbered beginning at ATG coding for first Met of human ICAM protein (x) PUBLICATION INFORMATION:
    (A) AUTHORS: Greve, J.M., G. Davis, A.M. Meyer, C.P. Forte, S.C. Yost, C.W. Marlor, M.E. Kamarck, and A. McClelland
    (B) TITLE: The Major Human Rhinovirus Receptor is ICAM-1
    (C) JOURNAL: Cell
    (D) VOLUME: 56
    (F) PAGES: 839-847
    (G) DATE: March 10, 1989
    (K) RELEVANT RESIDUES IN SEQ ID NO:10: FROM 1 TO 240

(xi) SEQUENCE DESCRIPTION: SEQ ID NO:12:

```
ACT  CAA  GGG  GAG  GTC  ACC  CGC  AAG  GTG  ACC  GTG  AAT  GTG  CTC  TCC            45
Thr  Gln  Gly  Glu  Val  Thr  Arg  Lys  Val  Thr  Val  Asn  Val  Leu  Ser
                     5                        10                       15

CCC  CGG  TAT  GAG  ATT  GTC  ATC  ATC  ACT  GTG  GTA  GCA  GCC  GCA  GTC            90
Pro  Arg  Tyr  Glu  Ile  Val  Ile  Ile  Thr  Val  Val  Ala  Ala  Ala  Val
                     20                       25                       30

ATA  ATG  GGC  ACT  GCA  GGC  CTC  AGC  ACG  TAC  CTC  TAT  AAC  CGC  CAG           135
Ile  Met  Gly  Thr  Ala  Gly  Leu  Ser  Thr  Tyr  Leu  Tyr  Asn  Arg  Gln
                     35                       40                       45

CGG  AAG  ATC  AAG  AAA  TAC  AGA  CTA  CAA  CAG  GCC  CAA  AAA  GGG  ACC           180
Arg  Lys  Ile  Lys  Lys  Tyr  Arg  Leu  Gln  Gln  Ala  Gln  Lys  Gly  Thr
                     50                       55                       60

CCC  ATG  AAA  CCG  AAC  ACA  CAA  GCC  ACG  CCT  CCC  TGAACCTATC                    223
Pro  Met  Lys  Pro  Asn  Thr  Gln  Ala  Thr  Pro  Pro
                     65                       70

CCGGGACAGG  GCCTCTT                                                                  240
```

(2) INFORMATION FOR SEQ ID NO:13:

(i) SEQUENCE CHARACTERISTICS:
        (A) LENGTH: 221 bases
        (B) TYPE: nucleic acid
        (C) STRANDEDNESS: single
        (D) TOPOLOGY: linear (ii) MOLECULE TYPE: cDNA to mRNA (iii) HYPOTHETICAL: no (iv) ANTI-SENSE: no (v i) ORIGINAL SOURCE:
                (A) ORGANISM: human
                (G) CELL TYPE: epithelial
                (H) CELL LINE: HeLa (v i i) IMMEDIATE SOURCE:
                (A) LIBRARY: cDNA library (i x) FEATURE:
                (A) NAME/KEY: partial human sICAM-1 cDNA to mRNA
                    sequence
                (B) LOCATION: sequence from human sICAM
                    corresponding to nucleotides 1384 to 1623 of
                    human ICAM lacking bp 1407 to 1426,
                    inclusive, of hICAM (x i) SEQUENCE DESCRIPTION: SEQ ID NO:13:

```
ACT  CAA  GGG  GAG  GTC  ACC  CGC  AAG  CCC  CCC  GGT  ATG  AGA  TTG  TCA              45
Thr  Gln  Gly  Glu  Val  Thr  Arg  Lys  Pro  Pro  Gly  Met  Arg  Leu  Ser
               5                        10                            15

TCA  TCA  CTG  TGG  TAGCAGCCGC  AGTCATAATG  GGCACTGCAG  GCCTCAGCAC                      97
Ser  Ser  Leu  Trp

GTACCTCTAT  AACCGCCAGC  GGAAGATCAA  GAAATACAGA  CTACAACAGG                             147

CCCAAAAAGG  GACCCCCATG  AAACCGAACA  CACAAGCCAC  GCCTCCCTGA                             197

ACCTATCCCG  GGACAGGGCC  TCTT                                                           221
```